United States Patent [19]

Harandi et al.

[11] Patent Number: 4,899,002

[45] Date of Patent: Feb. 6, 1990

[54] INTEGRATED STAGED CONVERSION OF METHANOL TO GASOLINE AND DISTILLATE

[75] Inventors: Mohsen N. Harandi, Lawrenceville; Hartley Owen, Belle Mead, both of N.J.

[73] Assignee: Mobil Oil Corp., New York, N.Y.

[21] Appl. No.: 223,657

[22] Filed: Jul. 25, 1988

[51] Int. Cl.[4] .......................... C07C 1/24; C07C 2/12
[52] U.S. Cl. ...................................... 585/312; 585/322; 585/329; 585/412; 585/469; 585/533; 585/606; 585/640; 585/733
[58] Field of Search ............... 585/402, 312, 408, 412, 585/418, 322, 640, 910, 329, 469, 533, 606, 733

[56] References Cited

U.S. PATENT DOCUMENTS

| | | | |
|---|---|---|---|
| 3,894,107 | 7/1975 | Butter et al. | 585/640 |
| 4,025,575 | 5/1977 | Chang et al. | 585/640 |
| 4,433,185 | 2/1984 | Tabak | 585/415 |
| 4,456,779 | 6/1984 | Owen et al. | 585/322 |
| 4,497,968 | 2/1985 | Wright et al. | 585/640 |
| 4,547,616 | 10/1985 | Avidan et al. | 585/639 |
| 4,579,999 | 4/1986 | Gould et al. | 585/640 |
| 4,654,453 | 3/1987 | Tabak | 585/322 |
| 4,689,205 | 8/1987 | Gould et al. | 585/312 |
| 4,788,042 | 11/1988 | Marsh et al. | 585/402 |
| 4,788,365 | 11/1988 | Harandi et al. | 585/312 |
| 4,788,366 | 11/1988 | Harandi et al. | 585/312 |
| 4,831,203 | 5/1989 | Owen et al. | 585/533 |
| 4,831,204 | 5/1989 | Kushnerick | 585/519 |

*Primary Examiner*—Anthony McFarlane
*Attorney, Agent, or Firm*—Alexander J. McKillop; Charles J. Speciale; L. Gene Wise

[57] ABSTRACT

A process for the increased production of olefinic gasoline is described incorporating the integration of olefins to gasoline conversion under moderate severity conditions in contact with zeolite type catalyst with oxygenates to olefins conversion. The product of the olefins to gasoline conversion is passed to an olefins to gasoline and distillate (MOGD) conversion zone for distillate production. Liquid recycle requirements, feed throughput and/or the number of MOGD fixed bed stages are reduced for the MOGD process and overall process costs are lowered. The process includes the use of common catalyst handling and regeneration steps for the integrated processes.

9 Claims, 2 Drawing Sheets

MOG POSITIONS IN MTO SHOWN BY SYMBOL

INTEGRATED STAGED CONVERSION OF METHANOL TO GASOLINE AND DISTILLATE

This invention relates to an integrated process for the conversion of methanol to olefinic gasoline in increased yield. More particularly, the invention relates to the conversion of methanol to gasoline and distillate through the sequential conversion of methanol to olefins and olefins to gasoline followed by further conversion to distillate boiling range products.

BACKGROUND OF THE INVENTION

In recent years the petroleum industry has witnessed the development of highly effective novel processes for the synthetic production of gasoline by the conversion of methanol over zeolite type catalyst, particularly medium pore size shape selective aluminosilicate catalyst. Further technological development has broadened the range of this technology to encompass the production of olefins, distillates and aromatics, based on $C_1$ chemistry and, in particular, methanol.

The ready availability of synthetic methanol from feedstocks such as natural gas, coal and wood provide a broad basis for the production of synthetic gasoline, distillates, olefins and aromatics. Various processes in the aforenoted field of technology are described in the following U.S. patents which are incorporated herein in their entirety by reference: U.S. Pat. Nos. 3,894,107 (Butter, et al); 3,928,483; 4,025,575; 4,252,479 (Chang, et al); 4,025,572 (Lago); 4,328,384 (Daviduk, et al); 4,547,616 (Avidan, et al); 4,450,311 (Right, et al); 3,960,978 and 4,021,502 (Plank, Rosinski and Givens); 4,150,062, 4,211,640 and 4,227,992 (Garwood, et al).

Conversion of olefins to gasoline and/or distillate product is disclosed in U.S. Pat. Nos. 3,960,978 and 4,021,502 (Givens, Plank and Rosinski) wherein gaseous olefins in the range of ethylene to pentene, either alone or in admixture with paraffins, are converted into an olefinic gasoline blending stock by contacting the olefins with a catalyst bed made up of ZSM-5 or related zeolite. In U.S. Pat. Nos. 4,150,062 and 4,227,992 Garwood et al discloses the operating conditions for the Mobil Olefin to Gasoline/Distillate (MOGD) process for selective conversion of $C_3+$ olefins. A fluidized bed process for converting ethene-containing light olefinic streams, sometimes referred to as the Mobil Olefin to Gasoline (MOG) process is described by Avidan et al in U.S. patent application No. 006,407, filed 23 Jan. 1987. The phenomena of shape-selective polymerization are discussed by Garwood in ACS Symposium Series No. 218, Intrazeolite Chemistry, "Conversion of $C_2$-$C_{10}$ to Higher Olefins over Synthetic Zeolite ZSM-5", 1983 American Chemical Society.

In the process for catalytic conversion of olefins to heavier hydrocarbons by catalytic oligomerization using an acid crystalline metallosilicate zeolite, such as ZSM-5 or related shape selective catalyst, process conditions can be varied to favor the formation of either gasoline or distillate range products. In the gasoline operating mode, or MOG reactor system, ethylene and the other lower olefins are catalytically oligomerized at elevated temperature and relatively low weight hourly space velocity (WHSV). Under these conditions ethylene conversion rate is greatly increased and lower olefin oligomerization is nearly complete to produce an olefinic gasoline comprising hexene, heptene, octene and other $C_6+$ hydrocarbons in good yield. At elevated pressure olefins are converted to heavier distillate range hydrocarbons as well as gasoline range hydrocarbons, the MOGD process. The production of distillate range products in the MOGD process requires significant process recycle and typically, multiple fixed bed reactors. Accordingly, practitioners in the field are challenged by the need to simplify the overall process to reduce cost while maintaining or improving upon product yields.

It is an object of the present invention to improve the overall operation and cost of the conversion of olefins to gasoline and distillate by process integration with methanol conversion processes.

It is a another object of the instant invention to effect further overall process improvements by the staged conversion of olefins to gasoline at moderate reaction conditions prior to conversion to higher distillate boiling range hydrocarbons.

SUMMARY OF THE INVENTION

It has been discovered that unexpected advantages are realized when olefins to gasoline conversion (MOG) is integrated into a combined staged process with the conversion of methanol to olefins (MTO) and the conversion of olefins to gasoline and distillate (MOGD) such that the conversion of lower olefins from MTO is conducted at the less severe MOG conditions and subsequently converted into distillate and gasoline under (MOGD) conditions. The novel process reduces the number of MOGD reactor vessels and lowers the amount of recycle required for the MOGD process. In addition, catalyst handling and regeneration steps can be combined for the MTO and MOG processes, leading to further significant savings.

More particularly, an integrated fluidized bed process for the conversion of lower oxygenates to olefinic gasoline has been discovered comprising the steps of:
  (a) contacting lower oxygenates feedstock with shape selective medium pore metallosilicate catalyst in an oxygenate to lower olefins conversion zone under oxygenates to lower olefins conversion conditions whereby an effluent stream rich in $C_4-$ olefins is produced;
  (b) cooling said effluent stream and passing said effluent stream to an olefins to gasoline conversion zone in contact with shape selective medium pore metallosilicate catalyst under olefins to gasoline conversion conditions whereby an olefins to gasoline conversion zone effluent stream comprising $C_5+$ olefinic hydrocarbons is produced;
  (c) passing spent catalyst from step (a) and step (b) to a common catalyst regeneration zone and oxidatively regenerating said spent catalyst;
  (d) recycling a first portion of regenerated catalyst to step (a) conversion zone and a second portion of regenerated catalyst to step (b) conversion zone.

The invention further includes a unique reactor system, comprising in combination:
  first vertical reactor means for containing a fluidized bed of zeolite-type catalyst under moderate severity reaction conditions;
  cooling means, receivably connected to a top portion of said first vertical reactor, for cooling reaction effluent therefrom;
  second vertical reactor means, receivably connected in a bottom portion to said cooling means, for containing a fluidized bed of zeolite-type catalyst at low severity reaction conditions;

catalyst regenerator vessel means, receivably connected to both first and second vertical reactor means, for regenerating spent catalyst therefrom;

indirect heat exchanger means connected to said first vertical reactor means in contact with the contents thereof for controlling the heat of reaction within said first reactor;

conduit means for admitting feedstock connected to a bottom portion of said first reactor means;

conduit means for withdrawing reaction product effluent stream connected to a top portion of said second reactor means.

DETAIL DESCRIPTION OF THE INVENTION

Figure 1:
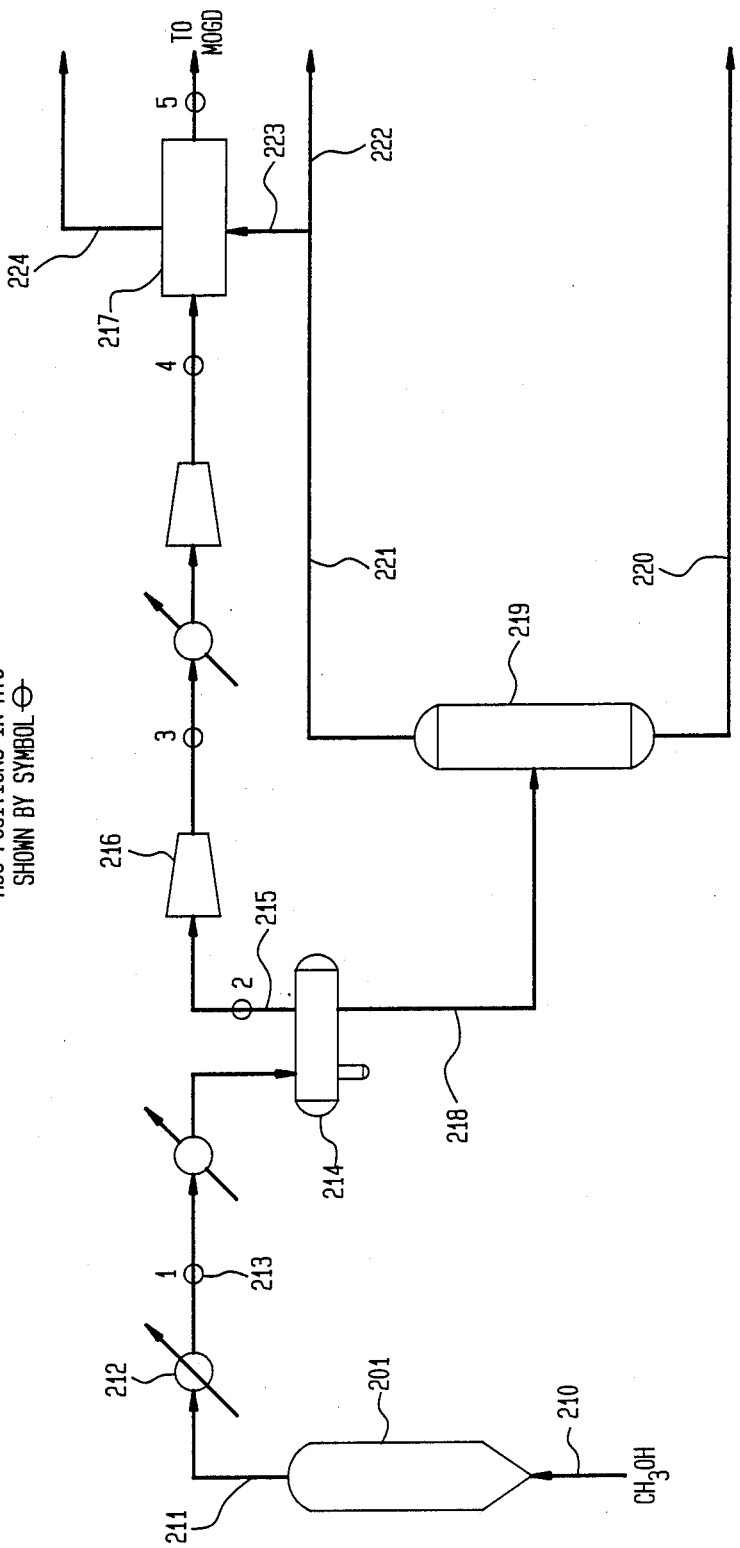
FIG. 1 is a flow diagram of the integrated process of the present invention.

The present invention involves the staged integration of $C_1$–$C_5$ oxygenates to olefins conversion (MTO) with olefins to gasoline (MOG) and olefins to gasoline and distillate (MOGD).

The present process is useful for the conversion of a number of differing oxygenated organic compounds into hydrocarbon products. The process is useful for the conversion of aliphatic compounds including lower alcohols such as methanol, ethanol and propanol, ethers such as DME and diethyl ether, ketones such as acetone, methyl ethyl ketone aldehydes such as acetaldehyde, esters such as methyl formate, methyl acetate and ethyl acetate, carboxylic acids such as acetic acid, butyric acid and their anhydrides e.g., acetic anhydride. Examples of conversions of such compounds may be found in U.S. Pat. Nos. 3,907,915, 3,894,107, 3,894,106, 3,894,103, 3,894,104, and 3,894,105 to which reference is made for details of the conversions.

The conversion of methanol or methanol equivalents is preferably catalyzed by a crystalline zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica:alumina ratio is correctly determined.

Preferred zeolites which have the specified values of Constraint Index and silica:alumina ratio include zeolites ZSM-5, ZSM-11, ZSM-12, ZSM-35, ZSM-38 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), 4,046,859 (ZSM-38) and European Patent Publication No. 15132. Reference is made to these patents for details of these zeolites, their preparation and properties. Of these zeolites, ZSM-5 is preferred.

The oligomerization catalyst preferred for use in olefins conversion includes the medium pore (i.e., about 5-7 angstroms) shape selective crystalline aluminosilicate zeolites having a silica to alumina ratio of about 20:1 or greater, a constraint index of about 1–12, and acid cracking activity (alpha value) of about 2–200.

Conversion of lower olefins, especially ethene, propene and butenes, over HZSM-5 is effective at moderately elevated temperatures and pressures. The conversion products are sought as liquid fuels, especially the $C_5+$ hydrocarbons. Product distribution for liquid hydrocarbons can be varied by controlling process conditions, such as temperature, pressure and space velocity. Olefinic gasoline (e.g., $C_5$–$C_9$) is readily formed at elevated temperature (e.g., 200° to about 400° C.) and moderate pressure from ambient to about 5500 kPa, preferably about 250 to 2900 kPa. Under appropriate conditions of catalyst activity, reaction temperature and space velocity, predominantly olefinic gasoline can be produced in good yield and may be recovered as a product. Operating details for typical olefin oligomerization units are disclosed in U.S. Pat. Nos. 4,456,779; 4,497,968 (Owen et al.) and 4,433,185 (Tabak), incorporated herein by reference.

The MOGD process converts light olefins to gasoline and distillate using relatively high activity ZSM-5 catalyst. Generally, the MOGD reaction section employs three fixed bed reactors in series. A super dense phase or gaseous phase fluid bed reactor can be used for MOGD as described in U.S. pending application Ser. No. 184,465, filed Apr. 20, 1988 and incorporated herein by reference. In the fixed bed MOGD reaction system, a significant amount of recycle is required. To reduce liquid recycle requirements and/or the required number of fixed bed reactors in series in the present invention, the MOG process is integrated with MOGD and light olefins are converted first to heavier olefins and olefinic gasoline. The MOG product is then fed to a MOGD unit for further conversion to gasoline and distillate.

MOG reaction conditions are low severity, i.e., temperature of about 200°–400° C., a weight hourly space velocity of 0.1–80 and an equilibrated catalyst activity of 2–10 alpha. The MTO process uses the same catalyst but higher severity conditions: temperature of 300°–540° C. and weight hourly space velocity of 0.1–5.0. It has been discovered that the two processes can be combined to convert methanol to olefinic gasoline which may then be upgraded in the MOGD process to high quality distillate. The benefits of using MOG in between MTO and MOGD are: reduction in the operating and investment cost of the MOGD unit; reduction in the cost of the MOG unit by combining MTO and MOG catalyst regenerating sections; reduction in the cost of the MOG unit by combining MOG and MTO catalyst handling facilities.

Referring to FIG. 1, a schematic diagram of the staged integrated process of the present invention is shown. The diagram illustrates the integration of the olefins to gasoline process (MOG) between the MTO and the MOGD process. There are five possible positions for the integration of the MOG unit in the overall process stream. The points of integration are shown as circles and numbered 1–5 in FIG. 1. Position 1 is the preferred position since the MTO reactor effluent can be cooled to MOG reaction temperature in the existing MTO reactor effluent cooler, thereby eliminating the need for the MOG feed preheat exchanger. In addition, the MTO catalyst recovery system can be used for the MOG reaction section. In FIG. 1, for the preferred embodiment, an oxygenated feedstock such as methanol is fed 210 to a fluidized bed methanol to olefins conversion unit 201. Effluent exiting the unit through conduit 211 is cooled 212 and passed to an MOG conversion reactor 213 where olefins are oligomerized to higher hydrocarbons. The effluent therefrom is separated in separator 214 and the vapor fraction is passed 215 for compression 216 and separation and recovery 217. The liquid portion is passed 218 to a fractionator 219 for separation of a heavy gasoline component 220 and light gasoline component 221. A portion of the light gasoline component is optionally recycled and a second portion 223 passed to recovery section 217. Light olefinic gasoline from recovery section 217 is passed to an MOGD unit for further conversion to heavier olefinic gasoline and distillate. A light gaseous fraction is recovered 224 from the recovery section. The gaseous fraction may include the $C_4-$ fraction if the $C_3-C_4$ olefins conversion in the MOG reactor is close to 100 percent; otherwise, the $C_3-C_4$ fraction is sent to the MOGD reactor for further upgrading to distillate. The heavy gasoline stream 220 can be sent to gasoline pool or to the MOGD reactor to further oligomerize the gasoline components to distillate. It may also be desirable to cut stream 220 as a light distillate stream which can be blended into the distillate pool after hydrotreating.

The integrated process described in FIG. 2 presents a highly advantageous opportunity to combine the catalyst regeneration functions and catalyst handling functions for both the MTO and MOG process since the same catalyst is used in both processes, albeit at different conditions. For instance, a common stripping zone for spent catalyst can be used. Also, catalyst can be circulated from the second reactor to the first reactor, removed from the first reactor and sent to the regenerator. Then, regenerated catalyst can be sent to the second reactor.

Figure 2B:
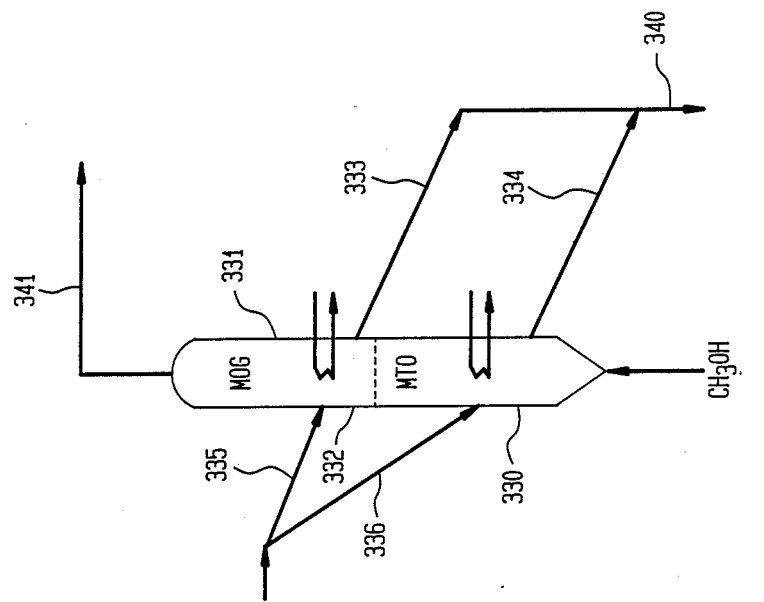
FIGS. 2A and 2B is a drawings of the unique reactor systems of the present invention.
Figure 2A:
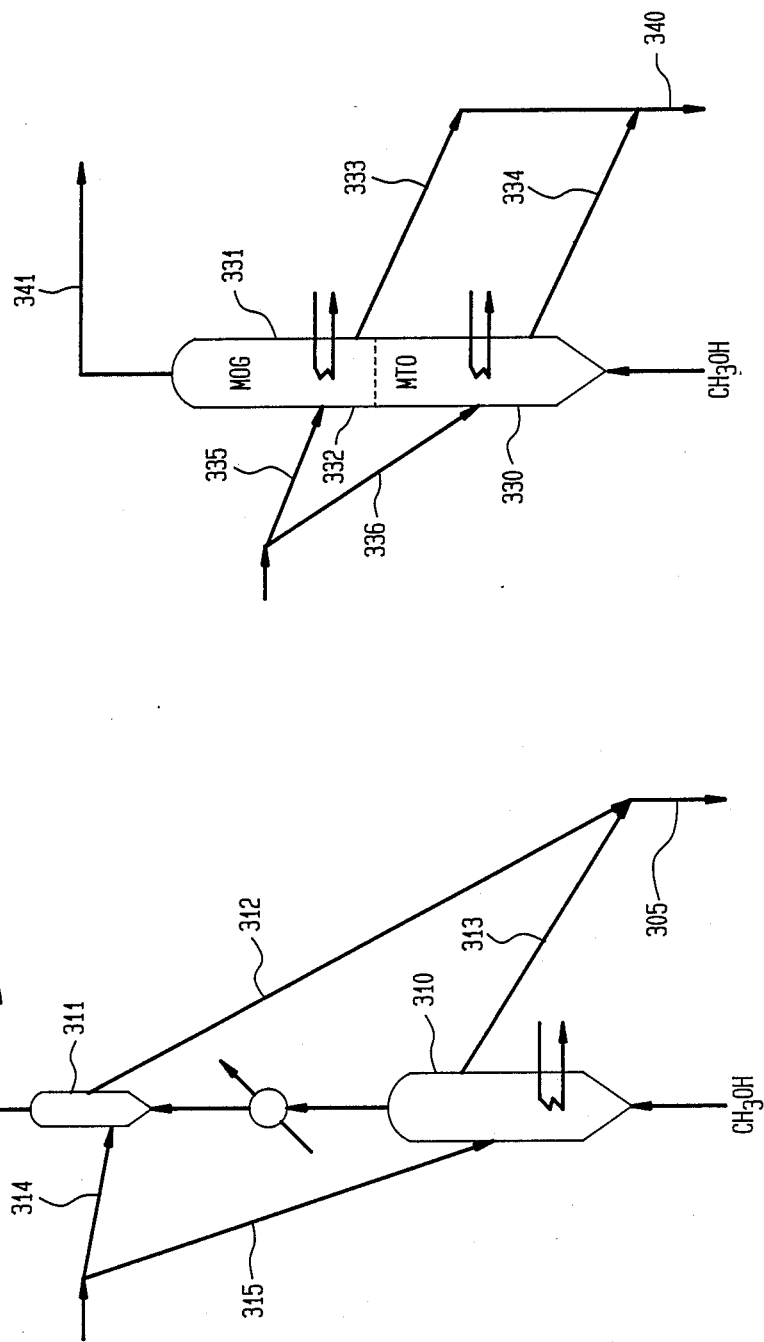

Referring to FIGS. 2A and 2B, two embodiments of the catalyst regenerator reactor system of the present invention are illustrated as A and B. Embodiment A includes two separate fluid bed vessels 310 and 311 for methanol conversion to olefins and olefins conversion to gasoline. Spent catalyst from the processes is passed 312–313 to a common regenerator vessel 305 and thence regenerated catalyst recycled 314–315 to the individual process units. MOG effluent 307 is passed to fines recovery.

In embodiment B of FIG. 3, a single vertical vessel configuration is utilized for both the fluidized bed methanol to olefins conversion 330 and the fluidized bed olefins to gasoline conversion 331. The two fluidized beds are separated by a grid member 332. Spent catalyst from both beds is passed 333 and 334 to a common catalyst regeneration vessel 340 and regenerated catalyst is returned 335–336 to the MTO and MOG conversion zones. MOG effluent 341 is passed to fines recovery.

In the foregoing novel reaction systems, the catalyst fines recovery system is preferably located on the MOG reactor effluent stream only. In this case provisions are made to circulate catalyst from the MOG to the MTO reactor employing various alternatives, such as by having MOG cyclone diplegs.

While the invention has been described by reference to certain preferred embodiments, there is no intention to limit the invention except as described in the following claims.

What is claimed is:

1. An integrated fluidized bed process for the conversion of $C_1-C_5$ oxygenate feedstock to olefinic gasoline range hydrocarbons and heavier distillate range hydrocarbons comprising the steps of:
    (a) contacting said $C_1-C_5$ oxygenate feedstock with shape selective medium pore metallosilicate catalyst in an oxygenate to light olefins conversion zone under oxygenate to light olefins conversion conditions whereby an effluent stream comprising $C_2+$ olefins is produced;
    (b) cooling said effluent stream and passing said effluent stream to an olefins to gasoline conversion zone in contact with shape selective medium pore metallosilicate catalyst under olefins to gasoline conversion conditions whereby $C_2+$ olefins are converted to gasoline comprising $C_5+$ olefinic hydrocarbons;
    (c) introducing said $C_5+$ hydrocarbons into an olefins to gasoline and heavier distillate range hydrocarbons conversion zone at increased pressure under olefins to gasoline and heavier distillate range hydrocarbon conversion conditions in contact with shape selective medium pore metallosilicate catalyst whereby olefinic gasoline and heavier distillate range hydrocarbons are produced without recycling $C_3-C_4$ hydrocarbons to said olefins to gasoline and heavier distillate range hydrocarbons conversion zone.

2. The process of claim 1 further comprising:
    passing spent catalyst from step (a) and step (b) to a common catalyst regeneration zone and oxidatively regenerating said spent catalyst;
    recycling a first portion of regenerated catalyst to step (a) conversion zone and a second portion of regenerated catalyst to step (b) conversion zone.

3. The process of claim 1 wherein step (a) effluent stream is cooled and separated in a liquid/vapor separator to provide hydrocarbon vapor and hydrocarbon liquid fractions; wherein said hydrocarbon vapor fraction is passed to step (b) conversion zone for olefins to gasoline conversion; wherein said hydrocarbon liquid fraction is passed to a fractionator whereby a heavy gasoline bottom fraction is separated and an overhead fraction is separated comprising olefinic hydrocarbons.

4. The process of claim 3 wherein said hydrocarbon vapor fraction is compressed before passing to step (b) conversion zone for conversion of olefins to gasoline comprising C5+ olefinic hydrocarbons.

5. The process of claim 3 wherein said hydrocarbon vapor fraction is cooled and fractioned before passing to step (b) conversion zone.

6. The process according to claim 1 wherein step (a) oxygenate to olefins conversion conditions comprise temperature between about 300° and 540° C. and pressure of about 120 to 1000 kPa.

7. The process of according to claim 1 wherein said olefins to gasoline conversion conditions comprise temperature between about 200° and 400° C. and pressure between about 120 and 5500 kPa.

8. The process according to claim 1 wherein said metallosilicate catalyst comprises ZSM-5 having an equilibrated average alpha value between about 2 and 20, a silica alumina ratio greater than 12 and a constraint index of about 1 to 12.

9. The process according to claim 1 wherein said $C_1$–$C_5$ oxygenate comprises methanol.

* * * * *